United States Patent
Huang et al.

(10) Patent No.: US 6,915,668 B2
(45) Date of Patent: Jul. 12, 2005

(54) WEARABLE ELECTRODE APPARATUS AND MANUFACTURE THEREOF

(75) Inventors: Hong-Hsu Huang, Taipei (TW); Cheng-Yi Chen, Taipei (TW); Chun-Jong Kuo, Taipei (TW)

(73) Assignee: King's Metal Fiber Technologies Co., LTD, Taipei (TW)

( * ) Notice: Subject to any disclaimer, the term of this patent is extended or adjusted under 35 U.S.C. 154(b) by 56 days.

(21) Appl. No.: 10/704,620

(22) Filed: Nov. 12, 2003

(65) Prior Publication Data

US 2004/0118166 A1 Jun. 24, 2004

(30) Foreign Application Priority Data

Dec. 19, 2002 (TW) ........................................ 91132536 A (51) Int. Cl.⁷ ................................................ D04B 1/22
(52) U.S. Cl. ........................ 66/171; 66/202; 66/169 R
(58) Field of Search ............................... 66/169 R, 170, 66/171, 202; 2/169, 200.1; 607/2, 46, 115, 142, 148; 219/211, 545

(56) References Cited

U.S. PATENT DOCUMENTS

| | | | |
|---|---|---|---|
| 4,753,088 A | * | 6/1988 | Harrison et al. ............... 66/202 |
| 4,878,148 A | * | 10/1989 | Hee ............................. 66/193 |
| 5,226,225 A | | 7/1993 | Bryan et al. |
| 5,374,283 A | | 12/1994 | Flick et al. |
| 5,636,378 A | * | 6/1997 | Griffith .......................... 2/455 |
| 6,145,551 A | * | 11/2000 | Jayaraman et al. ..... 139/387 R |
| 6,151,528 A | | 11/2000 | Maida |
| 6,381,482 B1 | * | 4/2002 | Jayaraman et al. ......... 600/388 |
| 6,414,286 B2 | * | 7/2002 | Rock et al. ................. 219/545 |
| 6,860,122 B2 | * | 3/2005 | Goldberg ..................... 66/202 |

* cited by examiner

Primary Examiner—Danny Worrell
(74) Attorney, Agent, or Firm—Troxell Law Office, PLLC (57) ABSTRACT

The invention provides a wearable electrode apparatus and manufacture thereof. The wearable electrode apparatus includes a garment and 2M terminals. The garment includes 2M electrically conductive portions. Each of the terminals is disposed on one of the 2M electrically conductive portions, respectively, for purpose of connection with an external apparatus. In particular, a semi-garment is first formed and cut out from a fabric according to a pattern of the garment. The electrically conductive portions are formed together with or after the formation of the semi-garment. Then, the semi-garment with the electrically conductive portions is formed into the garment.

16 Claims, 9 Drawing Sheets

WEARABLE ELECTRODE APPARATUS AND MANUFACTURE THEREOF

FIELD OF THE INVENTION

The present invention relates to a wearable electrode apparatus and manufacture thereof. In particular, a semi-garment is first formed and cut out from a fabric according to a pattern of a garment which is an essential of a wearable electrode apparatus according to the invention. The garment is then formed from the semi-garment.

BACKGROUND OF THE INVENTION

The bio-medical instruments for applying electric currents on human body are continuously developed and widely used, such as, the Transcutaneous Electrical Nerve Stimulator (TENS), the Electronic Muscle Stimulator (EMS) . . . , etc. One essential component of the mentioned-above medical instruments is the electrode apparatus. The research and design of the electrode apparatus also influence the application range of the above-mentioned medical instruments deeply. By the development of material science, the wearable electrode apparatus for the above mentioned medical instruments are designed for widening the application range.

One of the prior arts of the wearable electrode apparatus is about knitting a dense net structure from the carbon fibers, in order to form an electrode for contacting the human body. However, because of the brittle material property of the carbon fibers, the wearable electrode made by the carbon fibers has the disadvantages such as short service life, lower wash-resistance, and limited design model. For example, the wearable electrode apparatus can not be designed as the socks-like model. The fitting level of the electrode made by the carbon fibers is lower, and also the effect of applying currents on human body is lower.

The other prior art of the wearable electrode apparatus is about coating the conductive material (such as the silver glue) over the macromolecular base, further forming the electrode. The related prior art of this type is disclosed in the U.S. Pat. No. 5,374,283. Comparing the two above-mentioned types, this type is washable, but the washing frequency is still limited. The wearable electrode apparatus formed by coating the conductive material can be designed in various kinds of models. However, the complex model for fitting human contour is still unavailable, such as the socks-like model. The wearing comfort of the wearable electrode apparatus formed by coating the conductive material still should be improved.

The manufacturing processes of the wearable electrode apparatus of two mentioned-above types are much complex, and the manufacture costs are much higher.

SUMMARY OF INVENTION

It is, therefore, a primary objection of the present invention to provide a wearable electrode apparatus, and the wearable electrode apparatus satisfies the needs for developing the wearable electrode apparatus, such as comfortable to wear, easy to produce, low manufacturing cost, various design model, limitless washing frequency . . . , etc.

According to the first preferred embodiment of the invention, a fabric including 2N spaced electrically conductive fabric strips is first knitted, where N is natural number. The electrically conductive fabric strips are made of a yarn consisting of textile fibers and metal fibers. Then, according to a pattern of a garment, a semi-garment is cut out from the fabric. The semi-garment includes 2M electrically conductive portions formed from the 2N electrically conductive fabric strips, where M is a natural number less than or equal to N. Subsequently, each of the 2M electrically conductive portions of the semi-garment is provided with a respective terminal for connection with an external apparatus. Finally, the semi-garment with the terminals is fabricated into the garment as the wearable electrode apparatus.

According to the second preferred embodiment of the invention, 2M electrically conductive pieces are first prepared by cutting out from a first fabric made of a yarn consisting of textile fibers and metal fibers, where M is a natural number. Then, according to a pattern of a garment, a semi-garment is cut out from a second fabric. 2M predetermined and spaced portions, which each corresponds to one of the 2M electrically conductive pieces, are defined on the semi-garment. Subsequently, each of the electrically conductive pieces is mounted onto the corresponding portion thereof on the semi-garment. Afterwards, each of the electrically conductive pieces mounted on the semi-garment is provided with a respective terminal for connection with an external apparatus. Finally, the semi-garment with the terminals is fabricated into the garment as the wearable electrode apparatus.

These and other objectives of the present invention will no doubt become obvious to those of ordinary skill in the art after reading the following detailed description of the preferred embodiment, which is illustrated in the various figures and drawings.

DETAILED DESCRIPTION OF THE INVENTION

A wearable electrode apparatus according to the invention mainly includes a garment and 2M terminals where M is a natural number.

In particular, the garment is made from a semi-garment which includes 2M spaced electrically conductive portions. Each of the 2M terminals is disposed onto one of the 2M electrically conductive portions, respectively, for connection with an external apparatus. More particularly, the semi-garment is first formed and cut out from a fabric according to a pattern of the garment. The electrically conductive portions are formed together with or after the formation of the semi-garment. Then, the semi-garment with the electrically conductive portions is formed into the garment.

What follows will describe in detail the fabrication processes of the wearable electrode apparatuses regarding some preferred embodiments of the invention and sufficiently illustrate the characteristics, spirit and advantage of the invention.

Figure 1A:
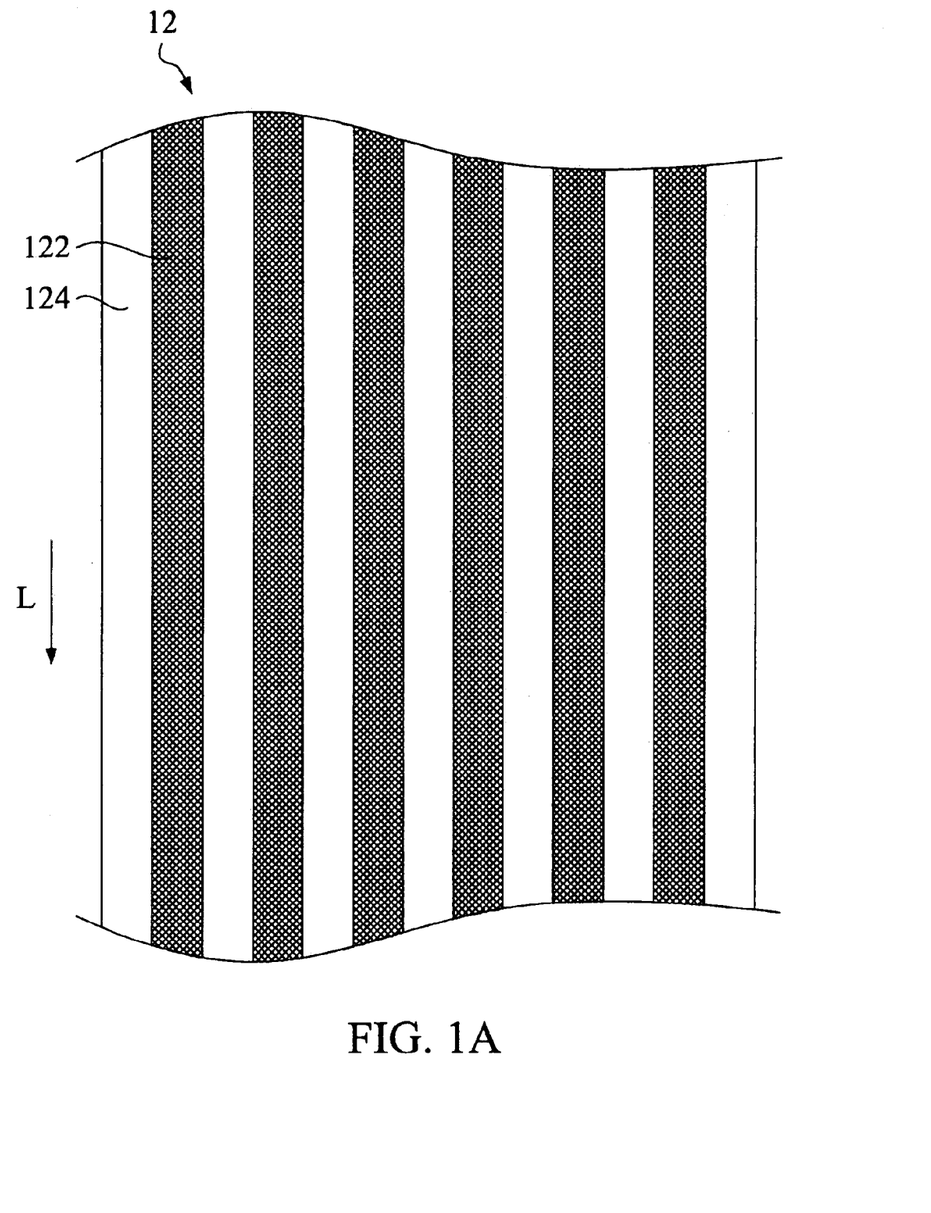
FIGS. 1A through 1D shows the manufacture process of a wearable electrode apparatus according to the first preferred embodiment of the invention.

Referring to FIGS. 1A through 1D, the manufacture process of a wearable electrode apparatus according to the first preferred embodiment of the invention is disclosed. As shown in FIG. 1A, first, a fabric 12, according to the invention, is knitted. In particular, the fabric 12 includes 2N spaced electrically conductive fabric strips 122 and K spaced electrically insulating fabric strips 124, where N and K are a natural number, respectively. The 2N electrically conductive fabric strips and the K electrically insulating fabric strips are disposed alternately, and stretched in a lengthwise direction approximately as the L direction in FIG. 1A. K can be equal to (2N−1), 2N, or (2N+1). The fabric 12 shown in FIG. 1A, which is an example that N is equal to 3 and K is equal to (2N+1), therefore, exhibits six electrically conductive fabric strips 122 and seven electrically insulating fabric strips 124.

More particularly, the 2N spaced electrically conductive fabric strips 122 are made of a yarn consisting of textile fibers and metal fibers.

In one embodiment, the metal fibers can be long or short fibers, the diameter of single metal fiber is 1 $\mu$m~30 $\mu$m. With respect to the selection of the material of the metal fibers, the properties of high corrosion-resistance and suitable impedance must be considered. In practical application, Ni—Cr alloy fibers and stainless steel fibers are the better choices.

In practical application, the percentage of the metal fibers in the yarn depends on the electric resistance of the electrically conductive portions 142, as desired. The reasonable range of the volume percentage of the metal fibers in single yarn is from 10% to 100%. The yarn can be made by a blending process or a twisting process.

Figure 1B:
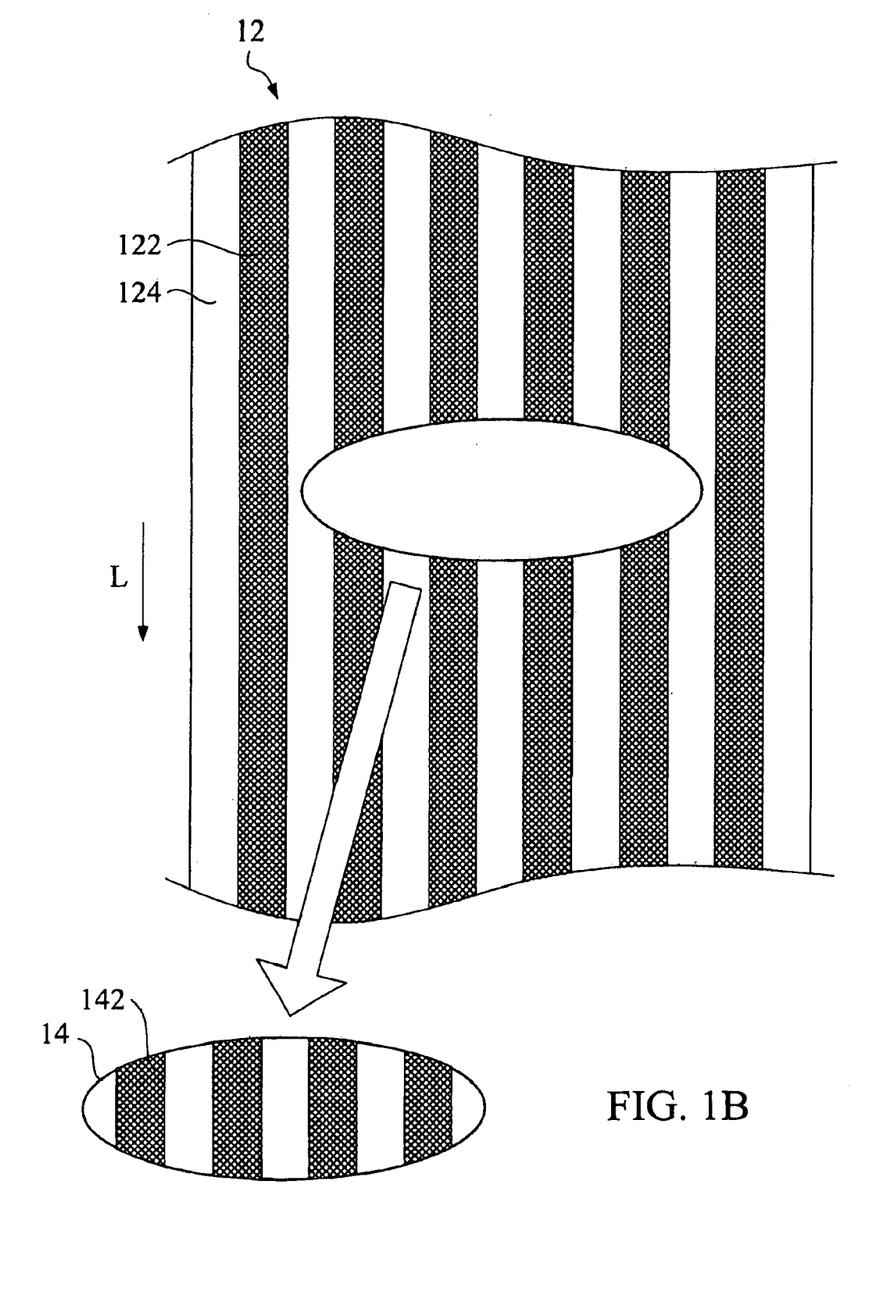

Subsequently, as shown in FIG. 1B, a semi-garment 14 is cut out from the fabric 12 in accordance with a pattern of a garment. The semi-garment 14 includes 2M electrically conductive portions 142 formed from the 2N electrically conductive fabric strips 122, where M is a natural number less than or equal to N. The semi-garment 14 shown in FIG. 1B, which is an example that M is equal to 2, therefore, exhibits four electrically conductive portions 142.

Figure 1C:
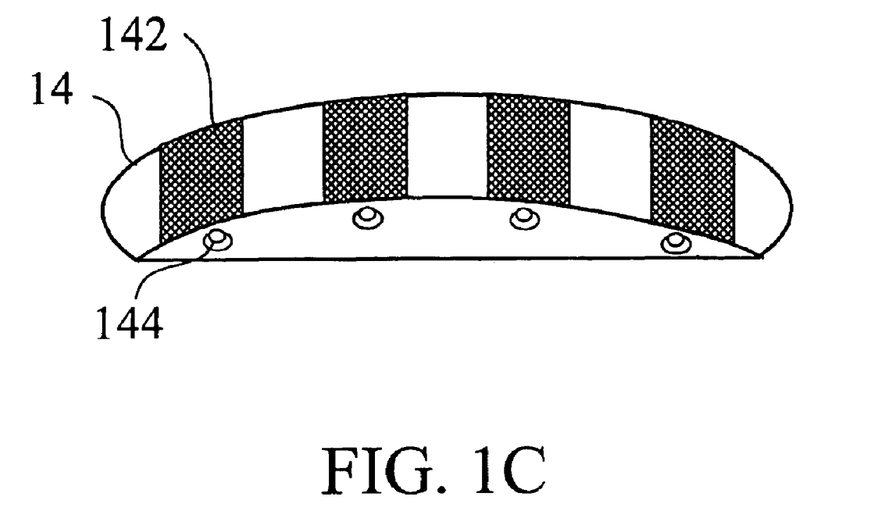

Afterwards, as shown in FIG. 1C, for purpose of connection with an external apparatus, 2M terminals 144, such as the metal buttons 144 shown in FIG. 1C, are mounted onto each of the 2M electrically conductive portions 142 of the semi-garment 14, respectively. The main function of the external apparatus is to provide and control current. Half of the 2M electrically conductive portions 142 connect the positive electrode of the external apparatus by the terminal 144. The others connect the negative electrode of the external apparatus by the terminal 144.

Figure 1D:
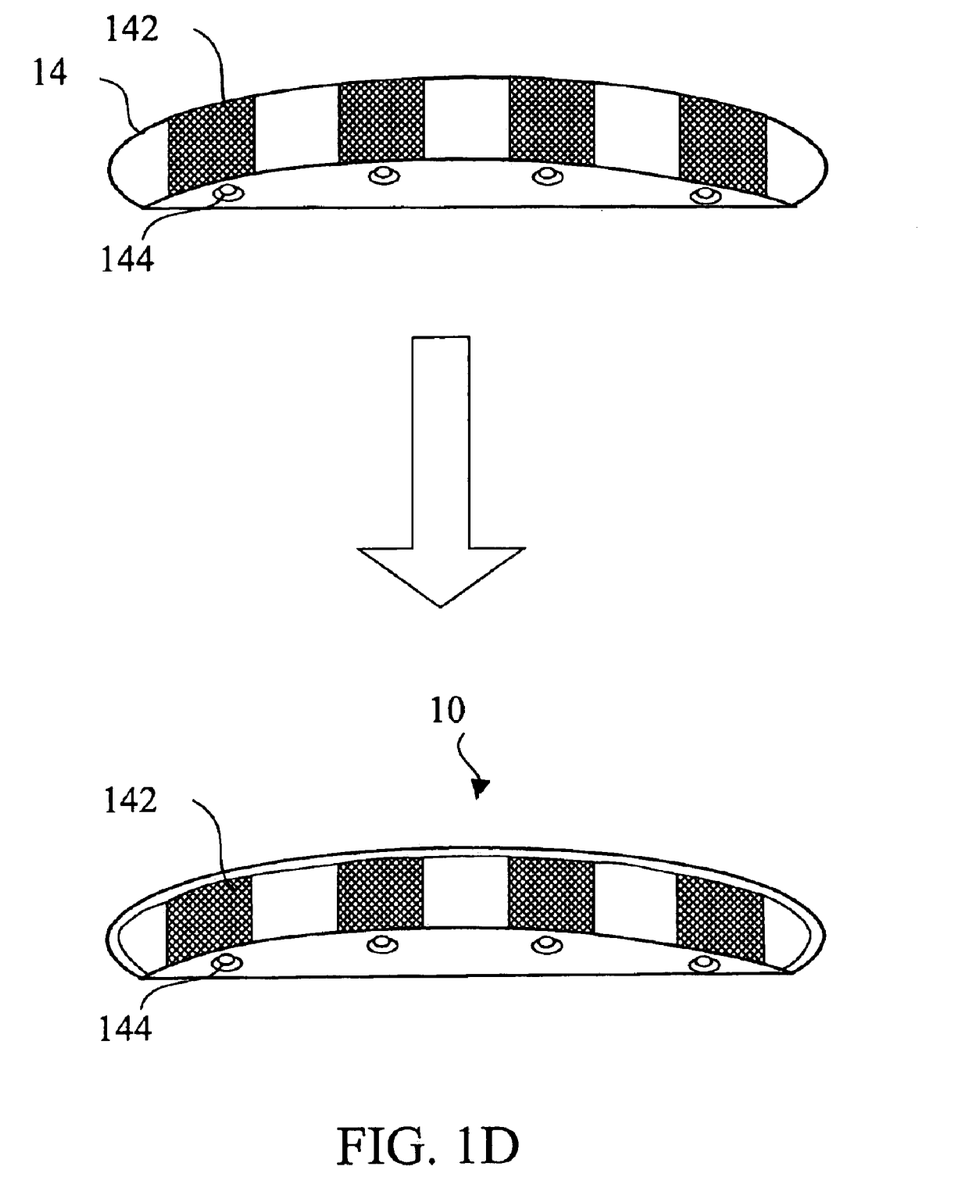

Finally, as shown in FIG. 1D, the semi-garment 14 with the terminals is formed into the garment 10 as the wearable electrode apparatus. The embodiment shown in FIG. 1D is further fabricating the semi-garment 14 into a tunic-like garment 10.

Figure 2A:
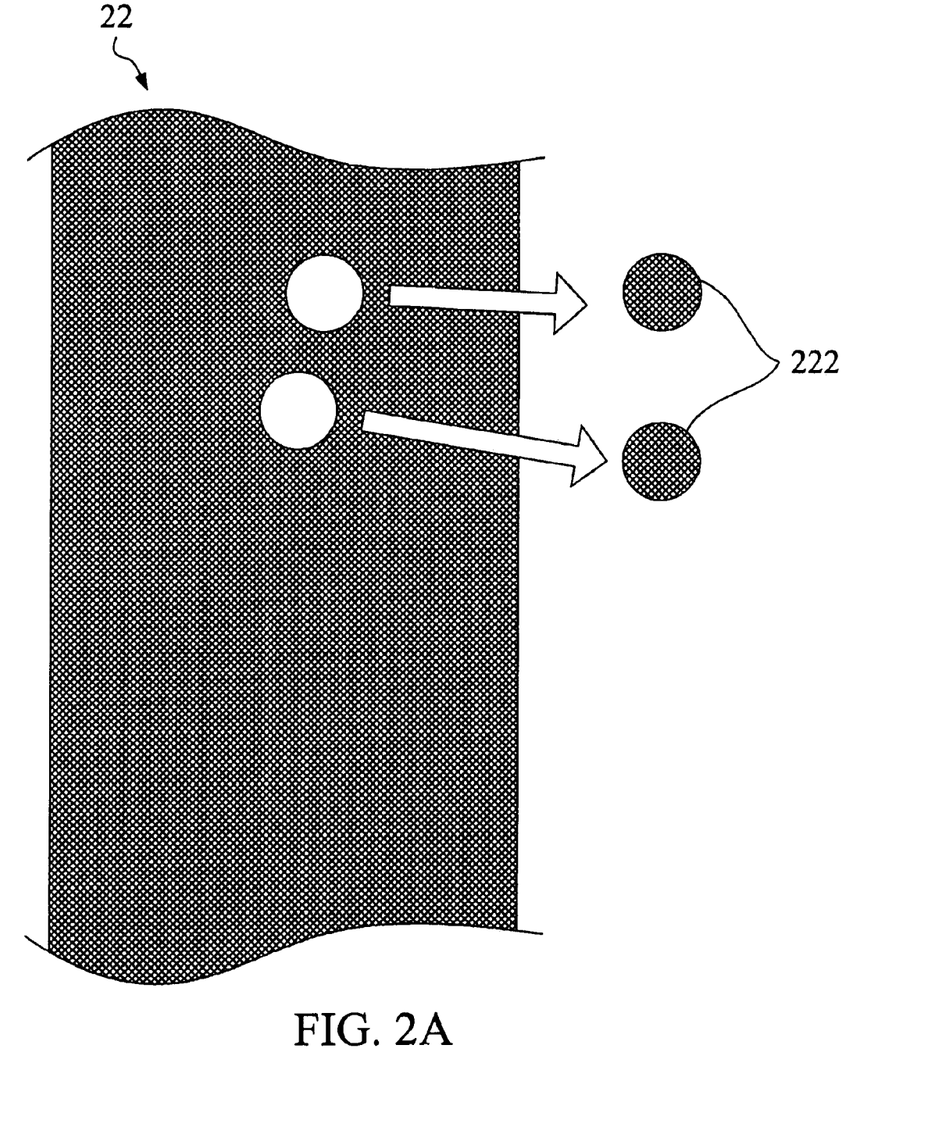
FIGS. 2A through 2E shows the manufacture process of a wearable electrode apparatus according to the second preferred embodiment of the invention.

Referring to FIGS. 2A through 2E, the manufacture process of a wearable electrode apparatus according to the second preferred embodiment of the invention is disclosed, and a. As shown in FIG. 2A, first, 2M electrically conductive pieces 222 are prepared by cutting out from a first fabric 22, where M is a natural number. In particular, the first fabric 22 is made of a yarn consisting of textile fibers and metal fibers. The electrically conductive pieces 222, shown in FIG. 2A, are an example that M is equal to 1.

In one embodiment, the metal fibers can be long or short fibers, the diameter of single metal fiber is 1 $\mu$m~30 $\mu$m. With respect to the selection of the material of the metal fibers, the properties of high corrosion-resistance and suitable impedance must be considered. In practical application, Ni—Cr alloy fibers and stainless steel fibers are the better choices.

In practical application, the percentage of the metal fibers in the yarn depends on the electric resistance of the electrically conductive portions 142, as desired. The reasonable range of the volume percentage of the metal fibers in single yarn is from 10% to 100%. The yarn can be made by a blending process or a twisting process.

Figure 2B:
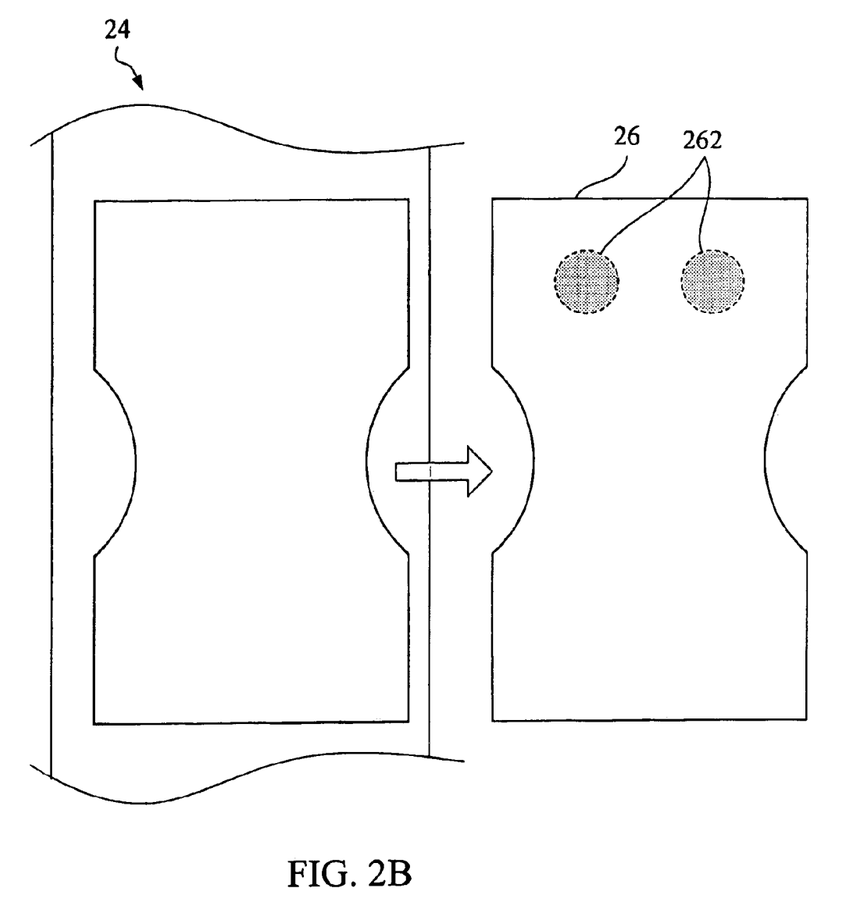

Subsequently, as shown in FIG. 2B, a semi-garment 26 is cut out from a second fabric 24 according to a pattern of a garment. In particular, 2M predetermined and spaced portions 262, which each corresponds to one of the 2M electrically conductive pieces, are defined on the semi-garment 26.

Figure 2C:
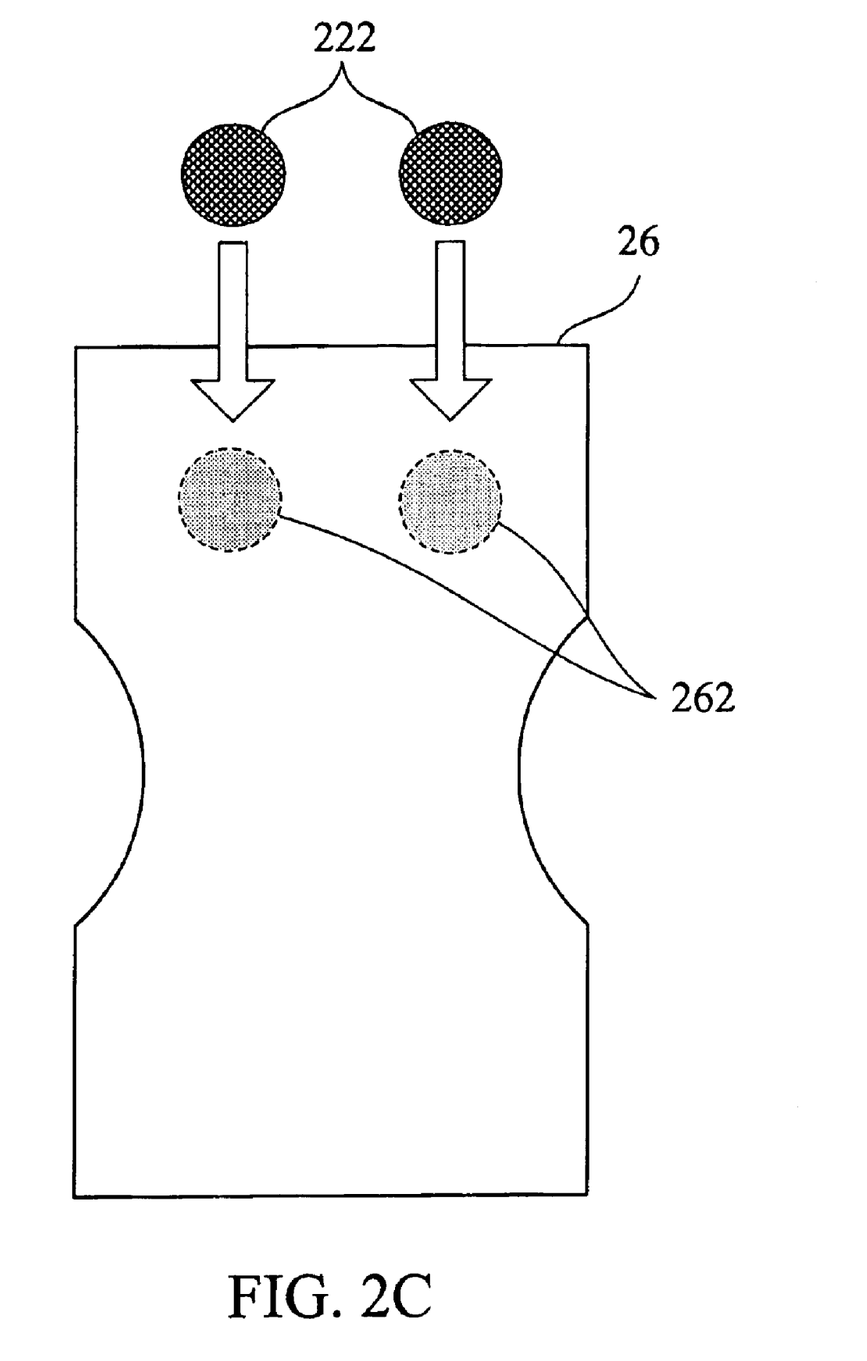

Then, as shown in FIG. 2C, each of the electrically conductive pieces 222 is mounted onto the corresponding portion 262 thereof on the semi-garment 26.

Figure 2D:
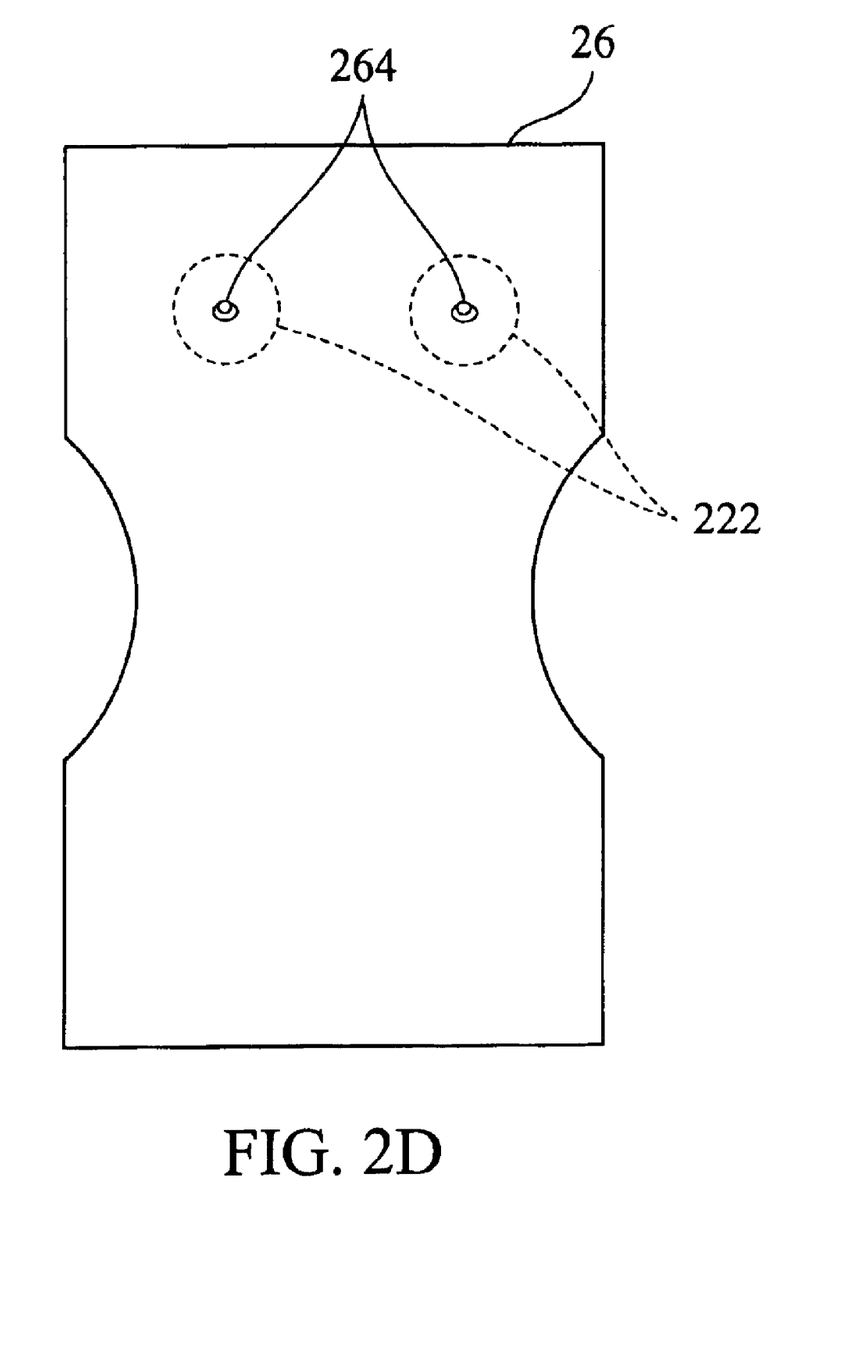

Afterwards, as shown in FIG. 2D, for purpose of connection with an external apparatus, 2M terminals 264, such as the metal buttons 264 shown in FIG. 2D, are mounted onto each of the 2M electrically conductive pieces 222 mounted onto the semi-garment 26, respectively. The main function of the external apparatus is to provide and control current. Half of the 2M electrically conductive pieces 222 connect the positive electrode of the external apparatus by the terminal 264, and the others connect the negative electrode of the external apparatus by the terminal 264.

Figure 2E:
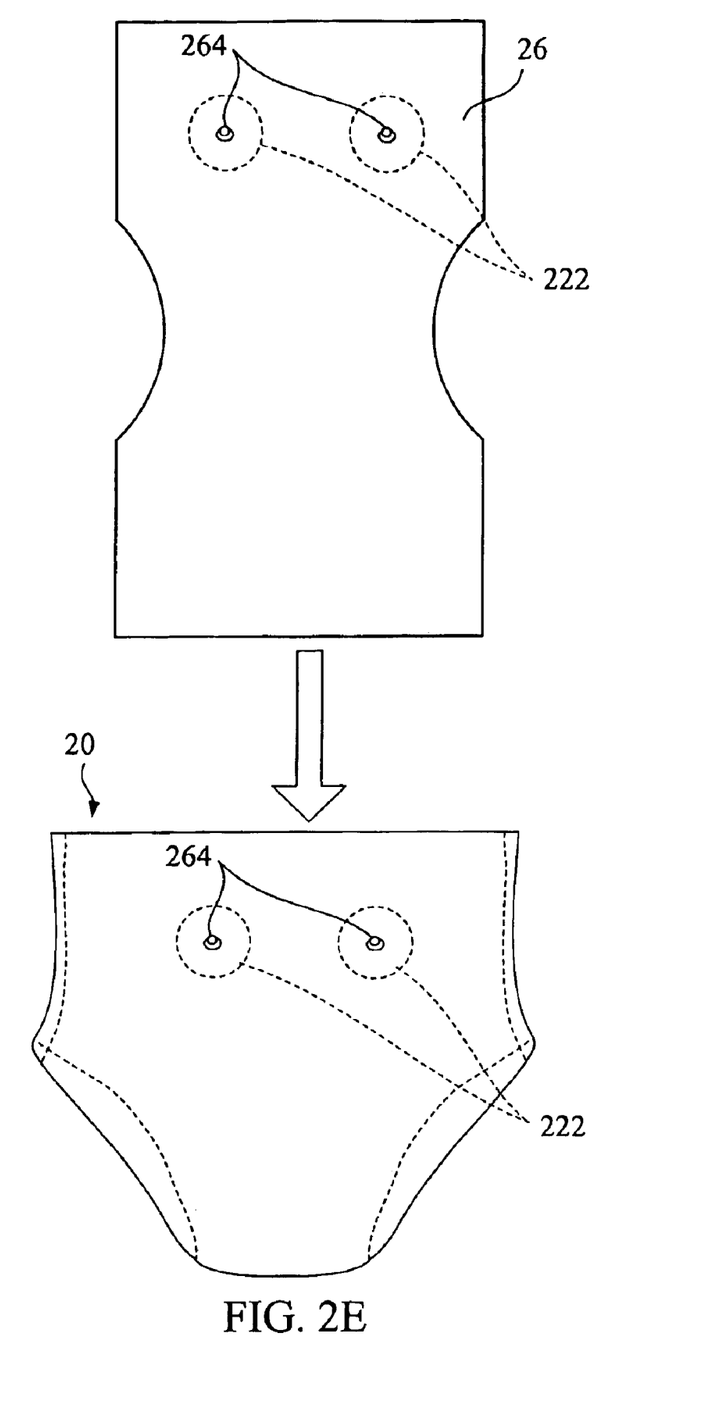

Finally, as shown in FIG. 2E, the semi-garment 26 with the terminals 264 is formed into the garment 20 as the wearable electrode apparatus. The embodiment shown in FIG. 2E is further fabricating the semi-garment 26 into an underpants-like garment 20.

Obviously, the wearable electrode apparatus of the present invention can be easily designed and fabricated into suitable models by the portion where to apply current. For example, the wearable electrode apparatus can be the ready-made garment model, the gloves-like model, the wristlet-like model, the socks-like model, . . . , etc. The wearable electrode apparatus of the present invention has the advantages of higher fitting level and more comfortable in comparison with the prior arts. The wearable electrode apparatus of the present invention fits the human body where to apply current, and the effect of applying current on human body is improving.

Obviously, the wearable electrode apparatus of the present invention has the advantages of easy-washing and higher washing frequency in comparison with the prior arts.

Obviously, the manufacturing process of the wearable electrode apparatus of the present invention has the advantages of lower manufacturing cost and shorter manufacturing time in comparison with the manufacturing process of the prior arts.

While the invention has been described in the preferred embodiment, it is understood that the words which have been used are words of description rather than words of limitation and that changes within the purview of the appended claims may be made without departing from the scope and spirit of the invention in its broader aspect.

What is claimed is:

1. A method of fabricating a wearable electrode apparatus, comprising the steps of:

knitting a fabric comprising 2N spaced electrically conductive fabric strips made of a yarn consisting of textile fibers and metal fibers, wherein N is a natural number;

according to a pattern of a garment, cutting out a semi-garment from the fabric, the semi-garment comprising 2M electrically conductive portions formed from the 2N electrically conductive fabric strips, wherein M is a natural number less than or equal to N;

providing each of the 2M electrically conductive portions of the semi-garment with a respective terminal for connection with an external apparatus; and fabricating the semi-garment with the terminals into the garment as said wearable electrode apparatus.

2. The method of claim 1, wherein the yarn contains the metal fibers in an amount between 10 to 100 volume percentage.

3. The method of claim 2, wherein the fabric also comprises K spaced electrically insulating fabric strips, the 2N electrically conductive fabric strips and the K electrically insulating fabric strips are disposed alternately, K is a natural number equal to or larger than (2N−1).

4. The method of claim 3, wherein the yarn is made by a blending process or a twisting process.

5. The method of claim 4, wherein the metal fibers are Ni—Cr alloy fibers or stainless steel fibers.

6. A wearable electrode apparatus, comprising:

a garment made from a semi-garment comprising 2M spaced electrically conductive portions, wherein M is a natural number;

2M terminals, each of the 2M terminals being disposed onto one of the 2M electrically conductive portions, respectively, for connection with an external apparatus.

7. The apparatus of claim 6, wherein the yarn contains the metal fibers in an amount between 10 to 100 volume percentage.

8. The apparatus of claim 7, wherein the yarn is made by a blending process or a twisting process.

9. The apparatus of claim 8, wherein the metal fibers are Ni—Cr alloy fibers or stainless steel fibers.

10. The apparatus of claim 9, wherein the semi-garment is formed by the steps of:

knitting a fabric comprising 2N spaced electrically conductive fabric strips made of a yarn consisting of textile fibers and metal fibers, wherein N is a natural number equal to or larger than M;

according to a pattern of the garment, cutting out the semi-garment from the fabric, wherein the 2M electrically conductive portions of the semi-garment are formed from the 2N electrically conductive fabric strips.

11. The apparatus of claim 10, wherein the fabric also comprises K spaced electrically insulating fabric strips, the 2N electrically conductive fabric strips and the K electrically insulating fabric strips are disposed alternately, K is a natural number equal to or larger than (2N−1).

12. The apparatus of claim 9, wherein the semi-garment is formed by the steps of:

preparing 2M electrically conductive pieces cut out from a first fabric made of a yarn consisting of textile fibers and metal fibers;

according to a pattern of the garment, cutting out the semi-garment from a second fabric, wherein 2M predetermined and spaced portions, which each corresponds to one of the 2M electrically conductive pieces, are defined on the semi-garment; and mounting each of the electrically conductive pieces onto the corresponding portion thereof on the semi-garment to form the 2M spaced electrically conductive portions of the semi-garment.

13. A method of fabricating a wearable electrode apparatus, comprising the steps of:

preparing 2M electrically conductive pieces cut out from a first fabric made of a yarn consisting of textile fibers and metal fibers, wherein M is a natural number;

according to a pattern of a garment, cutting out a semi-garment from a second fabric, wherein 2M predetermined and spaced portions, which each corresponds to one of the 2M electrically conductive pieces, are defined on the semi-garment;

mounting each of the electrically conductive pieces onto the corresponding portion thereof on the semi-garment;

providing each of the electrically conductive pieces mounted on the semi-garment with a respective terminal for connection with an external apparatus; and fabricating the semi-garment with the terminals into the garment as said wearable electrode apparatus.

14. The method of claim 13, wherein the yarn contains the metal fibers in an amount between 10 to 100 volume percentage.

15. The method of claim 14, wherein the yarn is made by a blending process or a twisting process.

16. The method of claim 15, wherein the metal fibers are Ni—Cr alloy fibers or stainless steel fibers.

* * * * *